(12) United States Patent
Nash (10) Patent No.: US 8,683,895 B2
(45) Date of Patent: Apr. 1, 2014

(54) SINGLE REVOLUTION SNAP ACTION DRIVE FOR SURGICAL FASTENERS

(75) Inventor: John E. Nash, Chester Springs, PA (US)

(73) Assignee: Kensey Nash Corporation, Exton, PA (US)

( * ) Notice: Subject to any disclaimer, the term of this patent is extended or adjusted under 35 U.S.C. 154(b) by 322 days.

(21) Appl. No.: 12/710,578

(22) Filed: Feb. 23, 2010

(65) Prior Publication Data

US 2011/0208169 A1  Aug. 25, 2011

(51) Int. Cl.
 *B25B 17/00* (2006.01)
 *A61B 17/00* (2006.01)

(52) U.S. Cl.
 USPC .............................. 81/463; 606/139; 81/57.29

(58) Field of Classification Search
 USPC .......... 81/463–466, 57.29, 57.13; 606/1, 139, 606/143; 608/1, 139, 143, 142
 See application file for complete search history.

(56) References Cited

U.S. PATENT DOCUMENTS

| | | |
|---|---|---|
| 791,766 A | 6/1905 | Furbish |
| 1,560,439 A | 11/1925 | Trenor |
| 2,023,235 A | 12/1935 | Lecount |
| 2,301,413 A | 11/1942 | Kilcup |
| 2,421,901 A | 6/1947 | Murad et al. |
| 2,474,626 A | 6/1949 | Gunning |
| 2,656,178 A | 10/1953 | Hughes, Jr. |
| 3,035,451 A | 5/1962 | O'Connell et al. |
| 3,049,018 A | 8/1962 | Lusskin et al. |
| 3,132,549 A | 5/1964 | Lee |
| 3,470,750 A | 10/1969 | Wetter |
| 3,519,046 A | 7/1970 | Pierce |
| 3,687,138 A | 8/1972 | Jarvik |
| 3,716,058 A | 2/1973 | Tanner, Jr. |
| 3,732,949 A | 5/1973 | Williams |
| 3,756,090 A | 9/1973 | Mella et al. |
| RE28,932 E | 8/1976 | Noiles et al. |
| 4,140,111 A | 2/1979 | Morrill |
| 4,154,122 A | 5/1979 | Severin |
| 4,204,541 A | 5/1980 | Kapitanov |
| 4,249,617 A | 2/1981 | Cox, Jr. |
| 4,448,194 A | 5/1984 | DiGiovanni et al. |
| 4,513,746 A | 4/1985 | Aranyi et al. |
| 4,522,207 A | 6/1985 | Klieman et al. |
| 4,524,650 A | 6/1985 | Marks |
| 4,578,551 A | 3/1986 | Lin |
| 4,595,007 A | 6/1986 | Mericle |
| 4,606,343 A | 8/1986 | Conta et al. |

(Continued)

FOREIGN PATENT DOCUMENTS

WO   WO 2009/114779 A2   9/2009

*Primary Examiner* — Hadi Shakeri
(74) *Attorney, Agent, or Firm* — Baker & Hostetler LLP (57) ABSTRACT

There is provided a device for the delivery of surgical fasteners. The device improves the penetration of the fasteners and reduces the effort required for a surgeon to hold opposing pressure in order to deploy the fastener. The device comprises a lever in mechanical cooperation with a resilient element for storing energy; a drive mechanism which cooperates with at least one surgical fastener; and a release mechanism for rapidly releasing stored energy from the resilient element to the drive mechanism. In certain embodiments, at least partial depression of the lever stores energy in the resilient element while release of the lever from the at least partial depressed position does not release the stored energy from the resilient element. Additionally, the drive mechanism converts stored energy from the resilient element upon activation of the release mechanism to deliver the at least one surgical fastener.

16 Claims, 11 Drawing Sheets

(56) References Cited

U.S. PATENT DOCUMENTS

| | | | |
|---|---|---|---|
| 4,611,595 A * | 9/1986 | Klieman et al. ............... 606/143 |
| 4,620,574 A | 11/1986 | Kilmer |
| 4,739,838 A | 4/1988 | Marks |
| 4,990,152 A | 2/1991 | Yoon |
| 5,024,565 A | 6/1991 | Pinand |
| 5,089,009 A | 2/1992 | Green |
| 5,098,004 A | 3/1992 | Kerrigan |
| 5,100,418 A | 3/1992 | Yoon et al. |
| 5,163,343 A | 11/1992 | Gish |
| 5,167,664 A | 12/1992 | Hodorek |
| 5,246,441 A | 9/1993 | Ross et al. |
| 5,289,731 A | 3/1994 | Womac |
| 5,300,081 A | 4/1994 | Young et al. |
| 5,320,630 A | 6/1994 | Ahmed |
| 5,356,064 A | 10/1994 | Green et al. |
| 5,363,726 A | 11/1994 | Smith |
| 5,398,861 A | 3/1995 | Green |
| 5,437,680 A | 8/1995 | Yoon |
| 5,478,353 A | 12/1995 | Yoon |
| 5,500,000 A | 3/1996 | Feagin et al. |
| 5,520,702 A | 5/1996 | Sauer et al. |
| 5,547,474 A | 8/1996 | Kloeckl et al. |
| 5,582,615 A | 12/1996 | Foshee et al. |
| 5,582,616 A | 12/1996 | Bolduc et al. |
| 5,590,741 A | 1/1997 | Storms |
| 5,607,436 A | 3/1997 | Pratt et al. |
| 5,645,209 A | 7/1997 | Green et al. |
| 5,662,683 A | 9/1997 | Kay |
| 5,728,116 A | 3/1998 | Rosenman |
| 5,730,744 A | 3/1998 | Justin et al. |
| 5,735,854 A | 4/1998 | Caron et al. |
| 5,743,456 A | 4/1998 | Jones et al. |
| 5,782,844 A | 7/1998 | Yoon et al. |
| 5,810,851 A | 9/1998 | Yoon |
| 5,810,882 A | 9/1998 | Bolduc et al. |
| 5,824,008 A | 10/1998 | Bolduc et al. |
| 5,830,221 A | 11/1998 | Stein et al. |
| 5,880,532 A | 3/1999 | Stopher |
| 5,893,305 A | 4/1999 | Liao |
| 5,904,696 A | 5/1999 | Rosenman |
| 5,911,722 A | 6/1999 | Adler et al. |
| 5,964,772 A | 10/1999 | Bolduc et al. |
| 5,972,022 A | 10/1999 | Huxel |
| 5,984,927 A | 11/1999 | Wenstrom, Jr. et al. |
| 6,010,513 A | 1/2000 | Tormala et al. |
| 6,015,410 A | 1/2000 | Tormala et al. |
| 6,036,701 A | 3/2000 | Rosenman |
| RE36,720 E | 5/2000 | Green et al. |
| 6,098,757 A | 8/2000 | Stephenson |
| 6,113,611 A | 9/2000 | Allen et al. |
| 6,241,736 B1 | 6/2001 | Sater et al. |
| 6,248,108 B1 | 6/2001 | Tormala et al. |
| 6,296,656 B1 | 10/2001 | Bolduc et al. |
| 6,319,270 B1 | 11/2001 | Grafton et al. |
| 6,328,746 B1 | 12/2001 | Gambale |
| 6,383,187 B2 | 5/2002 | Tormala et al. |
| 6,402,759 B1 | 6/2002 | Strong et al. |
| 6,425,900 B1 | 7/2002 | Knodel et al. |
| 6,447,524 B1 | 9/2002 | Knodel et al. |
| 6,457,625 B1 | 10/2002 | Tormala et al. |
| 6,508,830 B2 | 1/2003 | Steiner |
| 6,551,333 B2 | 4/2003 | Kuhns et al. |
| 6,551,343 B1 | 4/2003 | Tormala et al. |
| 6,562,051 B1 | 5/2003 | Bolduc et al. |
| 6,572,626 B1 | 6/2003 | Knodel et al. |
| 6,589,249 B2 | 7/2003 | Sater et al. |
| 6,592,578 B2 | 7/2003 | Henniges et al. |
| 6,663,038 B2 | 12/2003 | Juchem et al. |
| 6,722,232 B1 | 4/2004 | Day |
| 6,751,874 B2 | 6/2004 | Eldar |
| 6,755,836 B1 | 6/2004 | Lewis |
| 6,773,438 B1 | 8/2004 | Knodel et al. |
| 6,779,701 B2 | 8/2004 | Bailly et al. |
| 6,830,573 B2 | 12/2004 | Strong et al. |
| 6,837,893 B2 | 1/2005 | Miller |
| 6,884,248 B2 | 4/2005 | Bolduc et al. |
| 7,169,157 B2 | 1/2007 | Kayan |
| 7,229,452 B2 | 6/2007 | Kayan |
| 7,371,244 B2 | 5/2008 | Chatlynne et al. |
| 7,407,074 B2 | 8/2008 | Ortiz et al. |
| 7,485,124 B2 | 2/2009 | Kuhns et al. |
| 7,559,449 B2 | 7/2009 | Viola |
| 7,670,362 B2 | 3/2010 | Zergiebel |
| 7,686,822 B2 | 3/2010 | Shayani |
| 7,699,858 B2 | 4/2010 | Dahl et al. |
| 7,699,870 B2 | 4/2010 | Hart et al. |
| 2007/0250064 A1 | 10/2007 | Darois et al. |
| 2008/0275471 A1 | 11/2008 | Viola |
| 2008/0281353 A1 | 11/2008 | Aranyi et al. |

* cited by examiner

SINGLE REVOLUTION SNAP ACTION DRIVE FOR SURGICAL FASTENERS

TECHNICAL FIELD

Aspects of the present invention are directed to devices for applying surgical fasteners and, in particular, devices for rapidly and reproducibly applying surgical fasteners.

BACKGROUND

Operations involving the piercing of tissue benefit from control of the velocity of penetration. Tissue is visco-elastic and hence a rapid approach with a cutting instrument is beneficial to prevent tissue from moving away from the penetrator. For example, it is well known to employ scalpels having ultrasound superimposed, in order to cut with very low operator loads and to improve accuracy for initial incision. It would be beneficial therefore to control the velocity of approach of the distal point of a fastener intended for application in soft tissue. This would be particularly true when the configuration of the tissue relative to the screw applicator demands driving the screw away from normal to the tissue plane.

Biologically derived scaffold materials, generally known as extra cellular matrix (ECM), or other types of meshes present a particular challenge for fasteners, because they do not contain through holes for the fastener to pass through making them difficult to penetrate. If the fastener is applied too slowly to the mesh it would likely lead to the mesh material winding up into the threads of the fastener, thereby preventing effective penetration of the fastener. Preferably, the fastener pierces the mesh under rapid rotation and is rotated and advanced through the mesh material before it is distorted or reacts in response to the penetration forces.

Surgical repair of hernias with surgical mesh requires that the mesh be secured with sutures and/or fasteners to assure adequate fixation to the abdominal wall for repair and healing. In repairs such as ventral hernias, the mesh can require numerous fasteners applied using an applicator device with multiple fasteners to achieve the desired apposition of the mesh to the abdominal wall. One such device is an applicator disclosed in U.S. Pat. No. 5,582,616. Applicators of this type rotate the fastener into the mesh and underlying tissue as the surgeon squeezes the handle. The full stroke of the lever must be completed to fully seat the fastener. To achieve full seating of the fastener, the surgeon must oppose the end of the applicator on the exterior abdominal wall of the patient with his free hand, usually for several seconds, while depressing the lever. If the surgeon stops advancing the lever before full stroke, the fastener stops rotating and is not fully seated in the tissue. The surgeon must resume squeezing the lever to finish the fastener application so that it is fully seated. U.S. patent application Ser. No. 12/172,287 described an applicator having an actuator that is capable of storing energy for delivery of a fastener. The actuator is controllable in order to control or interrupt the release of the stored energy. The reference teaches a "dampening means" to control the rate of energy release to a smooth, deliberate action. It does not address the issues related to the delivery of fasteners at slow rates. Thus, during the time it takes to complete the sequence of events to insert a fastener, it is a likely that there would be movement of the applicator tip relative to the fixation site causing the misapplication of the fastener. Other applicators as described in U.S. Pat. No. 5,645,209 employ compressed gas to drive the applicator or as described in U.S. patent application Ser. No. 11/801,507, an electric motor. Although these applicators improve the control and speed of fastener application they require more component parts which add to weight, cost, reliability and shelf life of the devices.

Therefore, there is a need for an device that provides for instantaneous delivery of a surgical fastener with rapid rotational velocity in a reproducible manner without the drawbacks of traditional devices such as compressed air and electric motor devices.

SUMMARY

Aspects of the present invention are directed to a device for the delivery of surgical fasteners. The device comprises a lever in mechanical cooperation with a resilient element for storing energy, a drive mechanism which cooperates with the resilient element and at least one surgical fastener, and a release mechanism for rapidly releasing stored energy from the resilient element to the drive mechanism. In certain embodiments, at least partial depression of the lever stores energy in the resilient element; while release of the lever from the at least partial depressed position does not release the stored energy from the resilient element. In other embodiments, at least partial depression of the lever does not store energy in the resilient element if the lever is released prior to the release of energy to the drive mechanism. The drive mechanism converts stored energy from the resilient element upon activation of the release mechanism to deliver at least one surgical fastener.

In certain embodiments, the device is designed to deliver screw-like fasteners. In these embodiments, delivery is via the imparting of rotational and axial energy to the fastener. The device may be designed such that one complete depression of the lever stores sufficient energy to deploy one surgical fastener into tissue, whereas in other embodiments, one complete depression stores sufficient energy to deploy multiple fasteners.

The devices may further comprise a trigger for releasing the stored energy. Release of the stored energy may be selectably triggered upon complete depression of said lever. Additionally, the device may be equipped such that upon complete depression of the lever, the release mechanism must be triggered before further energy is stored. The device may also include a handle and an elongate tubular member, for containing a plurality of surgical fasteners, extending distally from the handle. The surgical fasteners may be iteratively deployable, such as for example, aligned along their axes.

In some embodiments, the device comprises an electric motor in mechanical cooperation with a resilient element for storing energy, rather than a lever. The electric motor upon being powered may direct energy into the resilient element.

Additional aspects of the present invention are directed to methods of securing a surgical mesh to a tissue using the devices of the present invention. Such methods may comprise providing a surgical mesh; providing a surgical fastener delivery system, and applying at least one fastener to secure the mesh to a tissue. The surgical fastener delivery system may be as described herein and may comprise an elongate tubular member containing a plurality of surgical fasteners, extending distally from the handle, and having a distal tip. The distal tip of the elongate tubular member may be positioned against the surgical mesh and the at least one fastener may secure the mesh to a tissue by depressing the moveable lever in relation to a stationary handle on the applicator.

A kit is also disclosed comprising a device for the delivery of surgical fasteners and multiple fastener cartridges. The kit may comprise various amounts of fastener cartridges, various sizes of fasteners, various types of fasteners, or a combination thereof. The cartridges may be disposable elongated tubular members containing multiple fasteners.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Other features of the subject matter are described below.

BRIEF DESCRIPTION OF THE DRAWINGS

The foregoing and other aspects of the present invention will become apparent from the following detailed description of the invention when considered in conjunction with the accompanying drawings. For the purpose of illustrating the invention, there are shown in the drawings embodiments that are presently preferred, it being understood, however, that the invention is not limited to the specific instrumentalities disclosed. The drawings are not necessarily drawn to scale. In the drawings.

DETAILED DESCRIPTION OF ILLUSTRATIVE EMBODIMENTS

Aspects of the present invention are directed to devices for the delivery of surgical fasteners. The devices provide for the delivery of fasteners in a fast, reproducible, uninterrupted motion. Such delivery may be facilitated through the storage of energy in a resilient element in mechanical cooperation with a lever. Once the resilient element has stored an amount of energy required to fully deploy at least one fastener, the energy may be released and the fastener deployed. Preferably the amount of energy required to fully deploy a fastener is consistent with one complete depression of the lever. In this embodiment, if, for example, a surgeon releases the lever in mid-stroke the spring remains partially wound, but the drive to the fastener is not released. A full stroke of the lever is required to release the spring and obtain propulsion of one fastener. This full stroke can be made in one smooth sweep of the lever or by building the stroke in several smaller increments. At the release of the spring and the consequent driving of one fastener, the mechanism automatically returns to its original position so that the next deployment is identical to the prior deployment. The energy storage capabilities of the resilient element avoids the difficulties of having to maintain the applicator in a fixed position over an extended period of time. Additionally, the devices of the present invention comprise a minimum number of parts so that they are light, reliable and can be manufactured at a relatively low cost.

Figure 1:
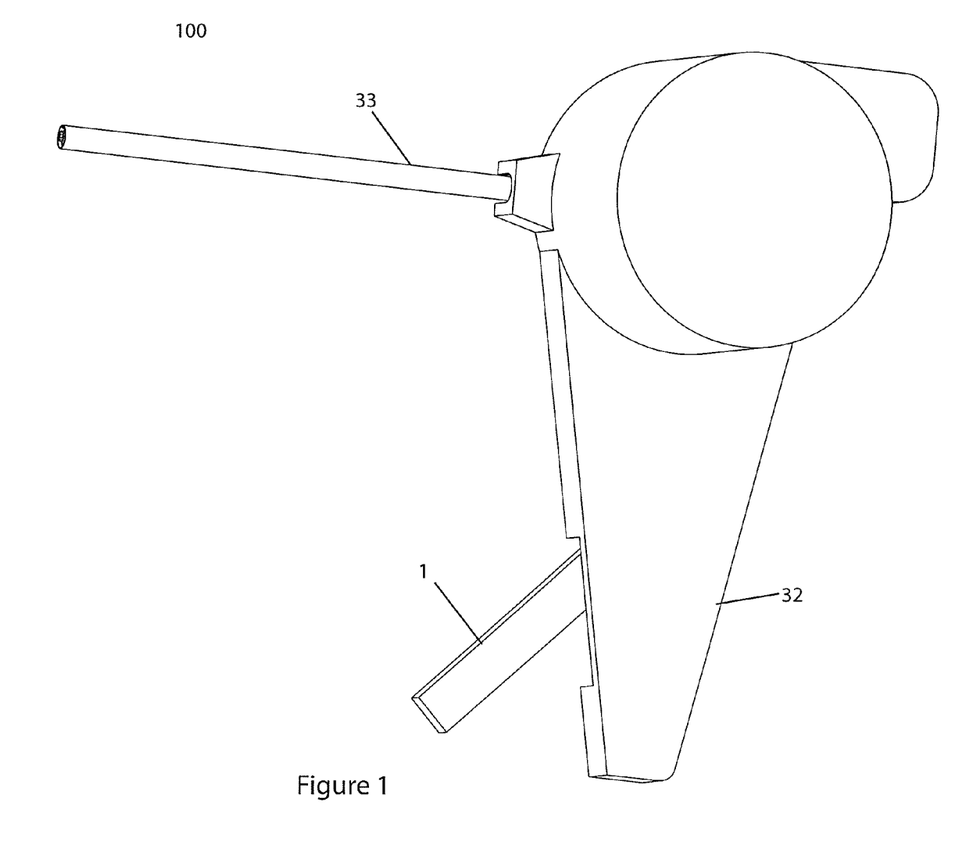
FIG. 1 is a perspective view of an embodiment of a device for the delivery of surgical fasteners.
Figure 2:
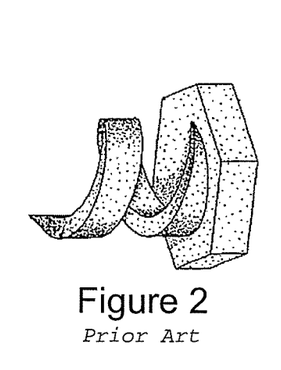
FIGS. 2-7 are examples of surgical fasteners that may be delivered by the fastener applier.
Figure 3:
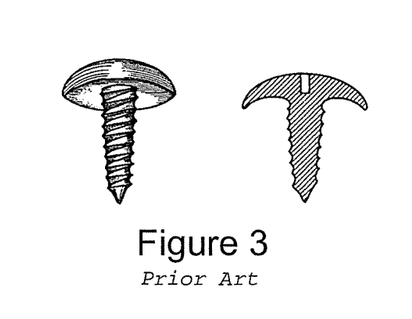
Figure 4:
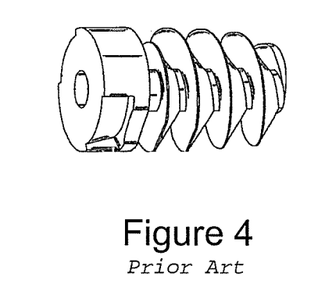
Figure 5:
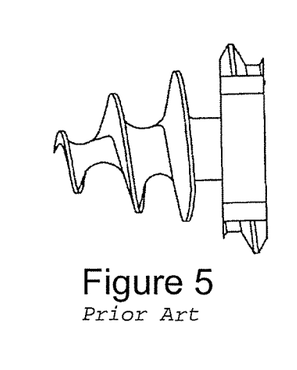
Figure 6:
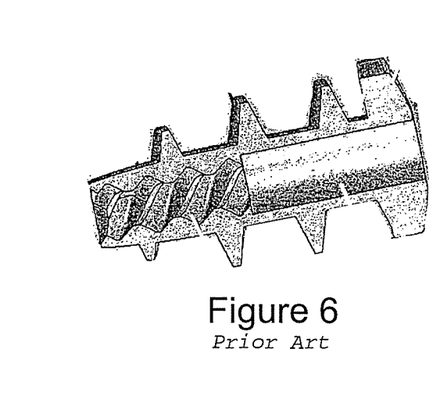
Figure 7:
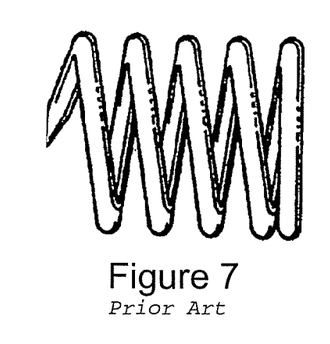

Embodiments of the invention are illustrated in FIGS. 1, 8-12. These embodiments are arranged to deliver fasteners that require rotation for penetration, and fixing of surgical repair materials and tissue. FIG. 1 shows a perspective view of a fastener applicator 100 comprising a handle 32, a lever 1, and a distal tubular structure 33. Fasteners, examples of which are shown in FIGS. 2-7, but not limited to only those shown, are housed within distal tubular structure 33. Ditsal tubular structure 33 may be reusable and can be reloaded with fasteners or it may be disposable. In a preferred embodiment the distal tubular structure is disposable and contains multiple fasteners. Fastener applicator 100 contains at least one fastener, but usually will hold from between 5 and 30 fasteners, so that multiple fasteners can be applied without the need for removing the applicator from the surgical site. In using the fastener delivery device, the fasteners' rotation may be achieved by a process involving the input of energy initiated by the actuation or depression of lever 1 relative to the stationary handle 32. Upon lever actuation or depression, the energy inputted may be transmitted, such as by a gear mechanism housed in handle 32, so that the energy may by captured and stored by increased tensioning or winding of a resilient element, such as a spring. The continued actuation of the lever will eventually reach a triggering point for a release mechanism, such as a cam and lever, such that the energy stored in the tensioned spring may be released and transmitted by a mechanism, such as a gear mechanism, to a rotator that is capable of rotating the fasteners for delivery. As the energy is released, the cam and lever of the release mechanism ensures that the spring unwinds by the same amount it was wound by the operation of the actuator assembly, so that after the complete delivery of one fastener, the actuator assembly and spring are back to their original energy state, and the actuator assembly is ready to be actuated once again to allow for the delivery of another fastener. In this manner, the repeated delivery of fasteners may be accomplished using the same delivery device, delivering one or more fasteners in a rapid, consistent manner.

The operation of the drive mechanism will now be described as illustrated in FIGS. 8-12. The energy to drive the fastener is generated by the movement of lever 1 but lever 1 motion does not directly drive the fastener. The energy developed with the hand lever motion is temporarily stored in spring 10 (see FIG. 11) through the winding mechanism of the drive train. The energy release is timed through the relationship of the gears, cams and followers so that it occurs at or near the end of the lever 1 stroke. In this manner the fastener is driven into tissue in an instantaneous motion.

Figure 8:
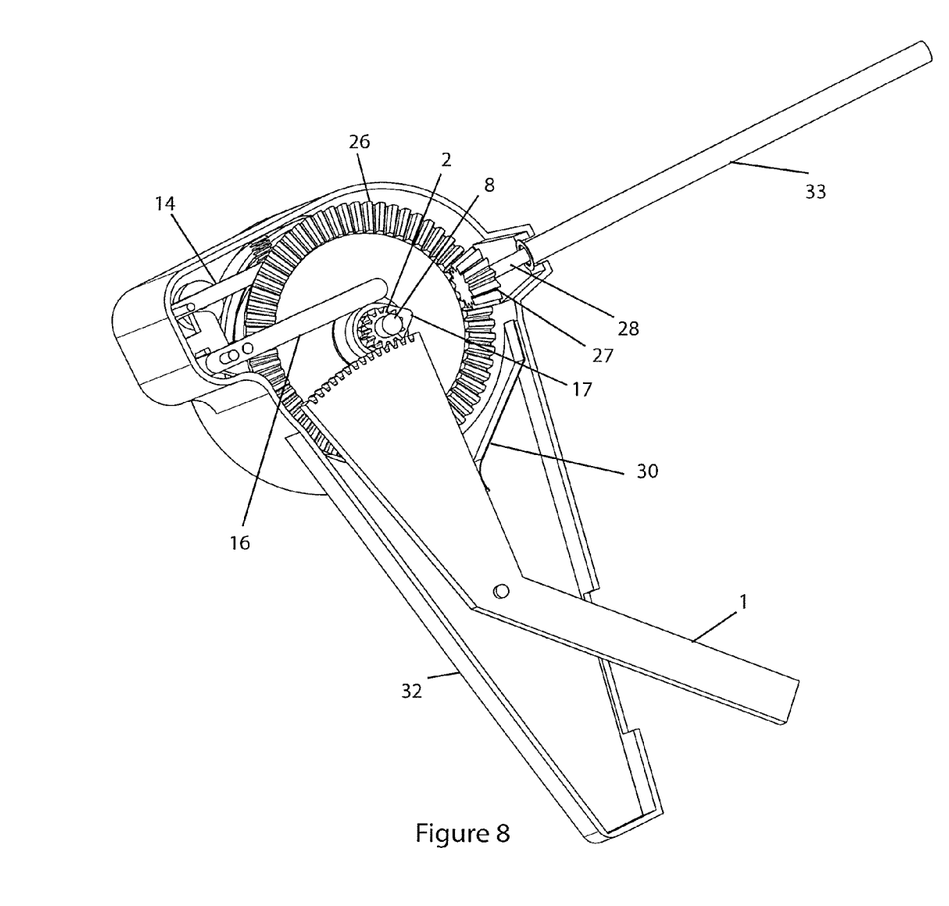
FIG. 8 is a partial internal right side view of the drive mechanism.
Figure 9:
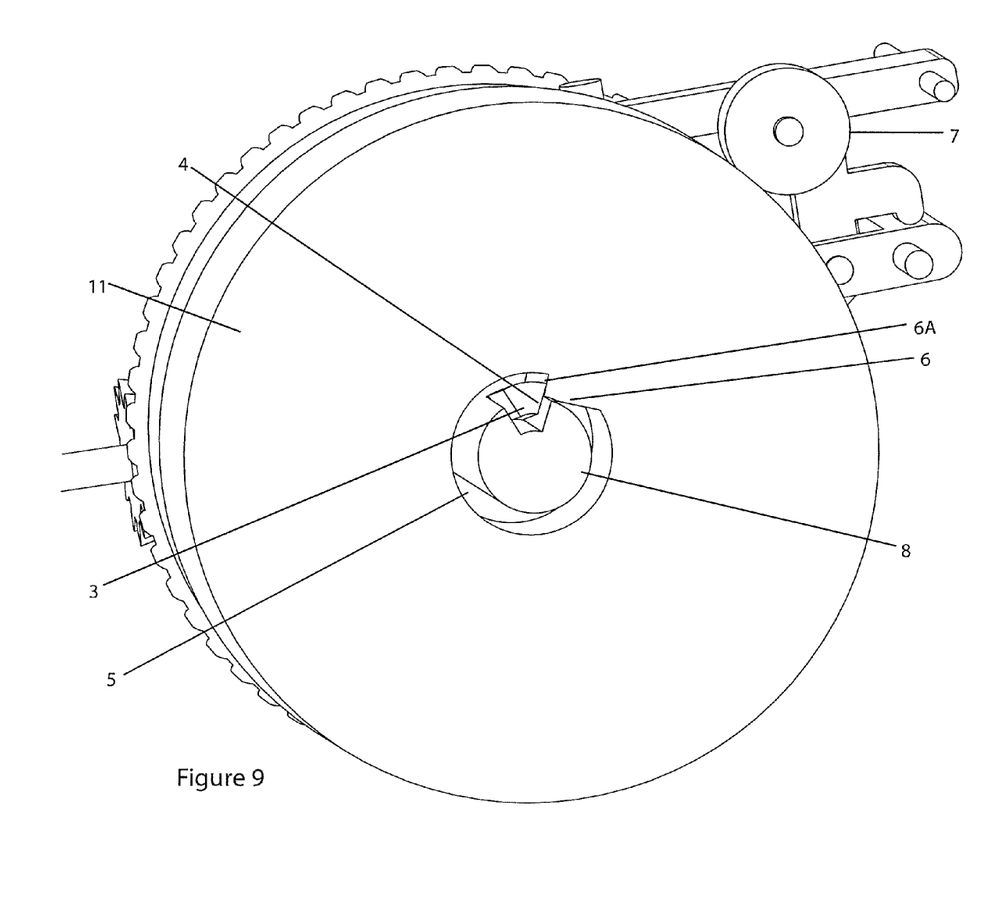
FIG. 9 is a detailed left side internal view of the drive mechanism.

As can be seen in FIG. 8, in delivering fasteners, the operator squeezes lever 1 compressing spring 30 which revolves pinion gear 2 in a counterclockwise direction. Pinion gear 2 drives shaft 8 in the same counterclockwise direction along with flexible tab 3, as depicted in FIG. 9, which is positioned on the opposite end of shaft 8. Flexible tab 3 (also depicted in FIG. 12) contains drive surface 4. Shaft 8 is piloted on first wheel 11, but does not revolve first wheel 11. Surface 4 on tab 3 engages buttress 6A at the end of slot 5 and hence turns first wheel 11 in the same direction as shaft 8 or clockwise as viewed in FIG. 9. Groove 5 extends almost completely around first wheel 11 except for ramp 6 and buttress 6A.

If the operator completely depresses lever 1, first wheel 11 will rotate exactly one complete revolution. If the operator relaxes his grip before complete depression, lever 1 reverses under influence of spring 30 and rotates counterclockwise, as viewed in FIG. 8, back to its home position. Surface 4 on flexible tab 3 on shaft 8 correspondingly can reverse in slot 5 with first wheel 11 held stationary by one-way clutch 7. First wheel 11 is permitted to rotate clockwise only, as viewed in FIG. 9, and prevented from rotating counterclockwise by one-way clutch 7.

If first wheel 11 has made one complete revolution and the operator releases his grip, surface 4 can rotate completely around slot 5 in the counterclockwise direction as viewed in FIG. 9, and flex below ramp 6 to once more enter slot 5 on the left hand side of the buttress 6A to reset for the next cycle. This mechanism ensures that first wheel 11 can move only one complete revolution when the operator pulls the handle full stroke.

Figure 10:
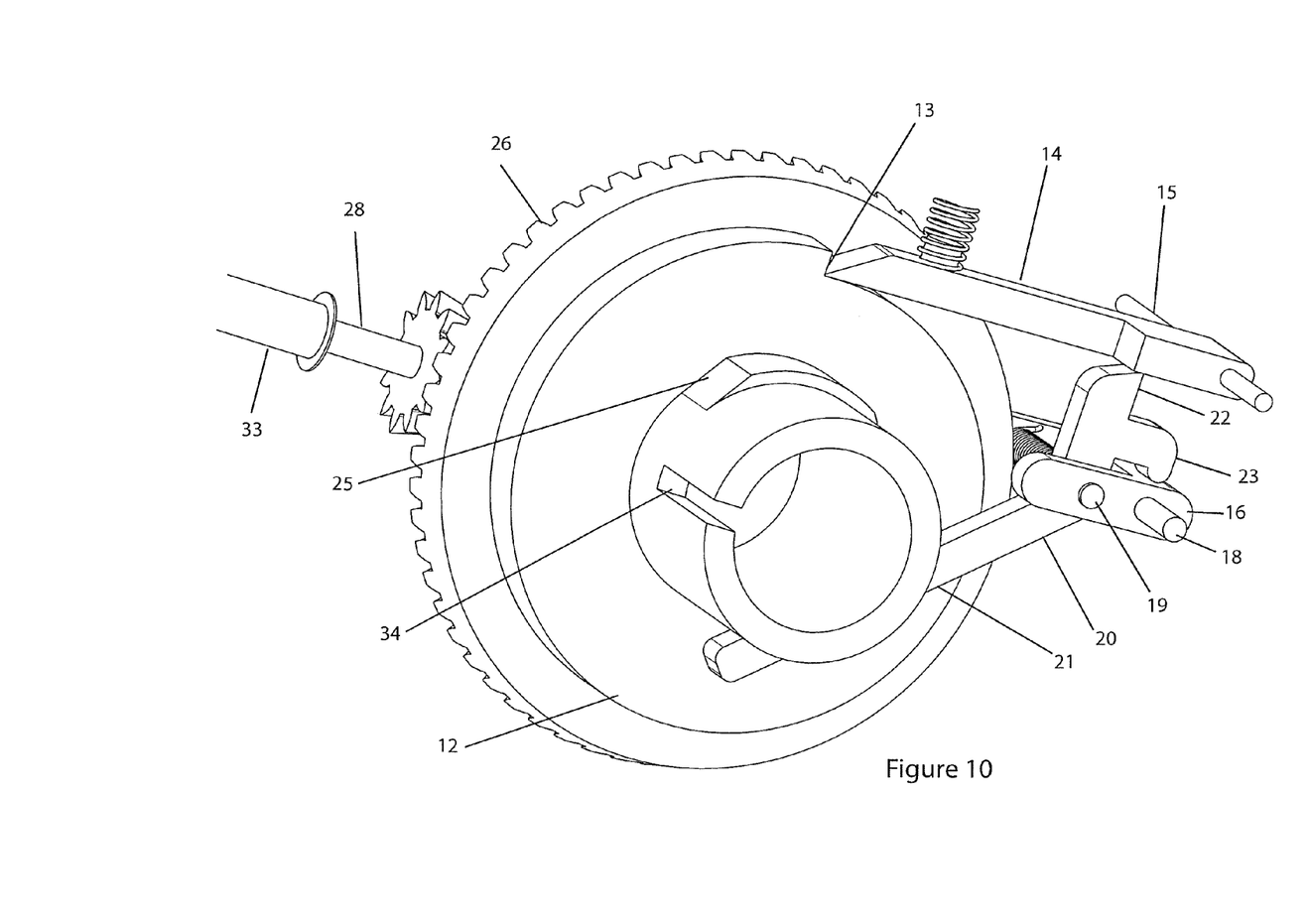
FIG. 10 is a view from the left side with the resilient element and wheel removed to show a partial internal view of the timing mechanism.
Figure 11:
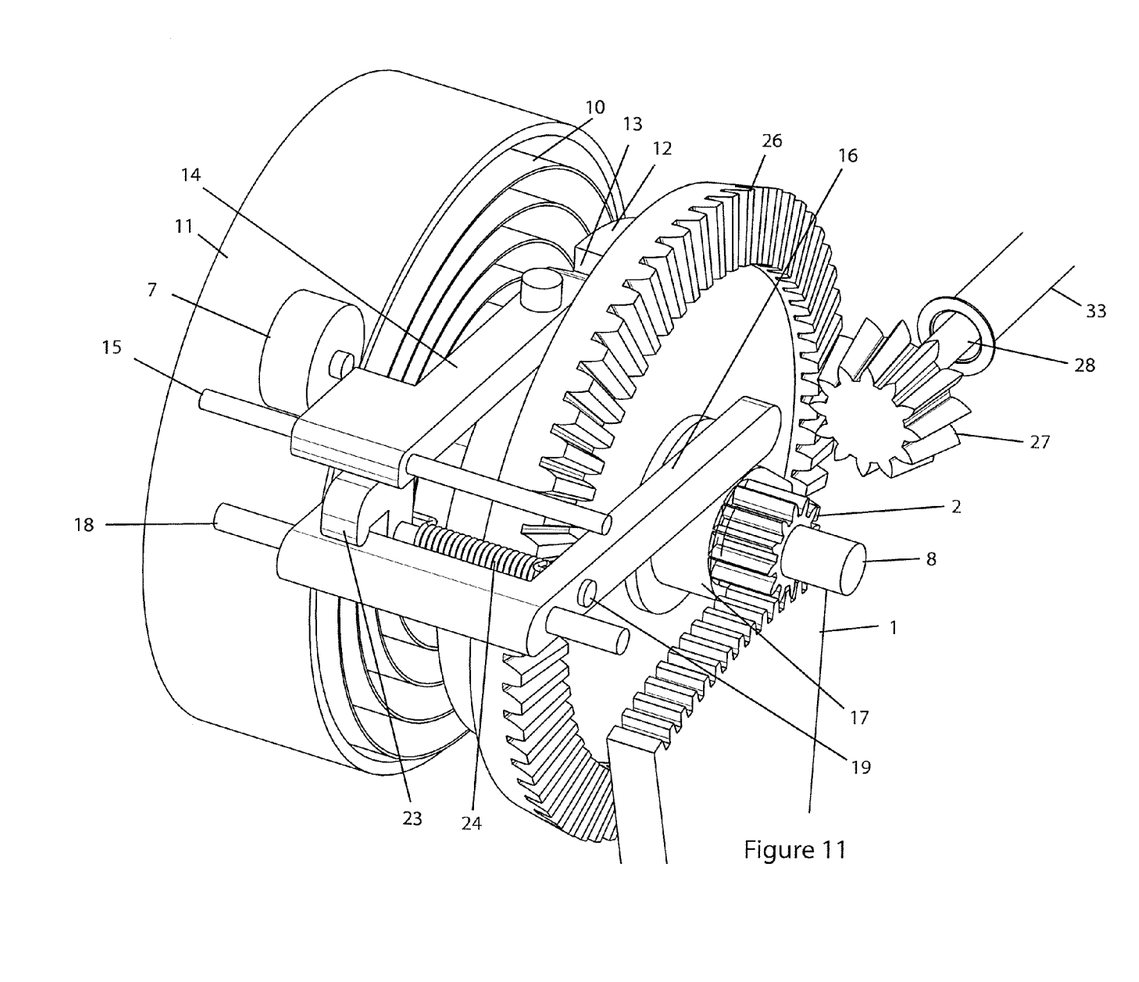
FIG. 11 is a perspective rear view of the drive mechanism without the external housing.

Mainspring 10, as seen in FIG. 11, may be wound within first wheel 11, with the mainspring outside end attached to first wheel 11 (e.g., fixed through a slot in the wheel body, or glued, welded, fastened or otherwise affixed to the wheel) and the mainspring inside end attached to the axle of second wheel 12 at slot 34, of FIG. 10. First wheel 11 winds mainspring 10 in the counterclockwise direction, as viewed in FIG. 11, and in so doing second wheel 12 is also driven counterclockwise by the spring but is held from turning by sprag link 14 at notch 13, FIG. 10. Sprag link 14 is pivoted to ground at 15, that is, the pivot point is in a fixed position relative to the outer case of the delivery instrument.

Link 16 is a 'U'-shaped link having a right hand arm, as viewed in FIG. 11, resting against cam 17. 'U'-shaped link 16 further provides for a floating pivot 19 on which compound link 20 rides, and a ground pivot 18. As depicted in FIG. 10, compound link 20 has a cam follower arm 21 resting against cam 25, which in turn is part of the second wheel 12. Compound link 20 also has stop arm 23 and strut arm 22. Stop arm 23 acts as a rotational stop to prevent compound link 20 from rotating clockwise relative to 'U'-shaped link 16, as seen in FIG. 10. Strut arm 22 acts as the actuator to raise sprag link 14. Torsion spring 24, as seen in FIG. 11, is fastened to 'U'-shaped link 16 in order to bias stop 23 against 'U'-shaped link 16.

Figure 12:
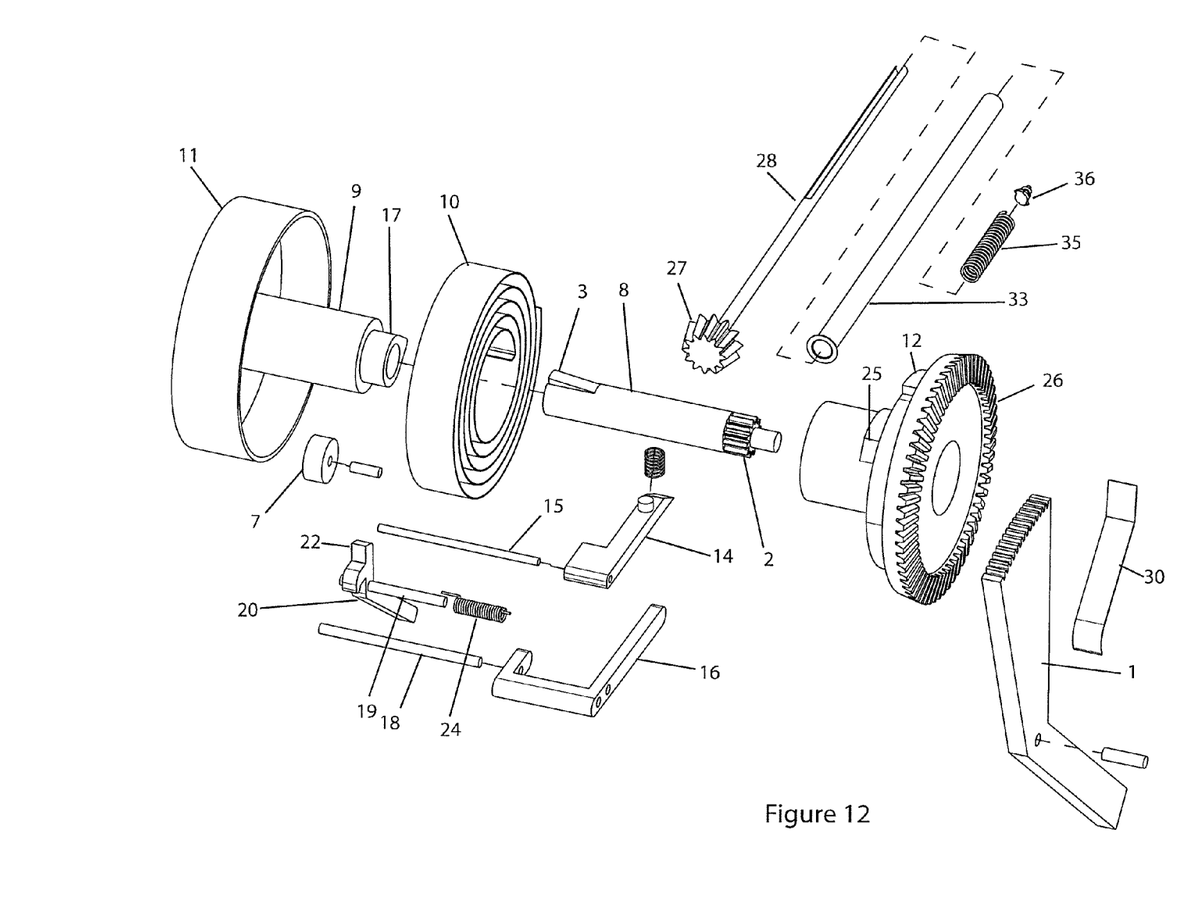
FIG. 12 is an exploded view of the drive mechanism.

As can be seen in exploded view of FIG. 12, the first wheel 11 is integral with second shaft 9 that passes through second wheel 12 and is attached to cam 17. As first wheel 11 turns, rotating shaft 9, cam 17 starts to lift the right hand arm of 'U'-shaped link 16, just as first wheel 11 completes one turn.

Compound link 20 is arranged to pivot on 'U'-shaped link 16, and may then cause strut arm 22 to lift sprag link 14 clear of notch 13, thus releasing wheel 12 to rotate.

As wheel 12 revolves, after release, cam 25 lifts cam follower arm 21 of compound link 20, in turn moving strut arm 22 in the counterclockwise direction, as viewed in FIG. 10. This motion disengages strut arm 22 from lifting sprag link 14 so that wheel 12 may be stopped by the falling sprag link 14 re-engaging notch 13 of second wheel 12.

Every time one revolution of first wheel 11 occurs, even though it may take considerable time to complete the one revolution, second wheel 12 will snap one revolution under influence from mainspring 10. Furthermore, for each time second wheel 12 revolves, the mainspring 10 unwinds one turn, and every time the first wheel 11 revolves one turn, the mainspring 10 is wound up one turn. Mainspring 10 can be pre-wound, for example 3 turns at assembly and then the spring will cycle between 4 and 3 turns as the device is actuated.

Figure 13:
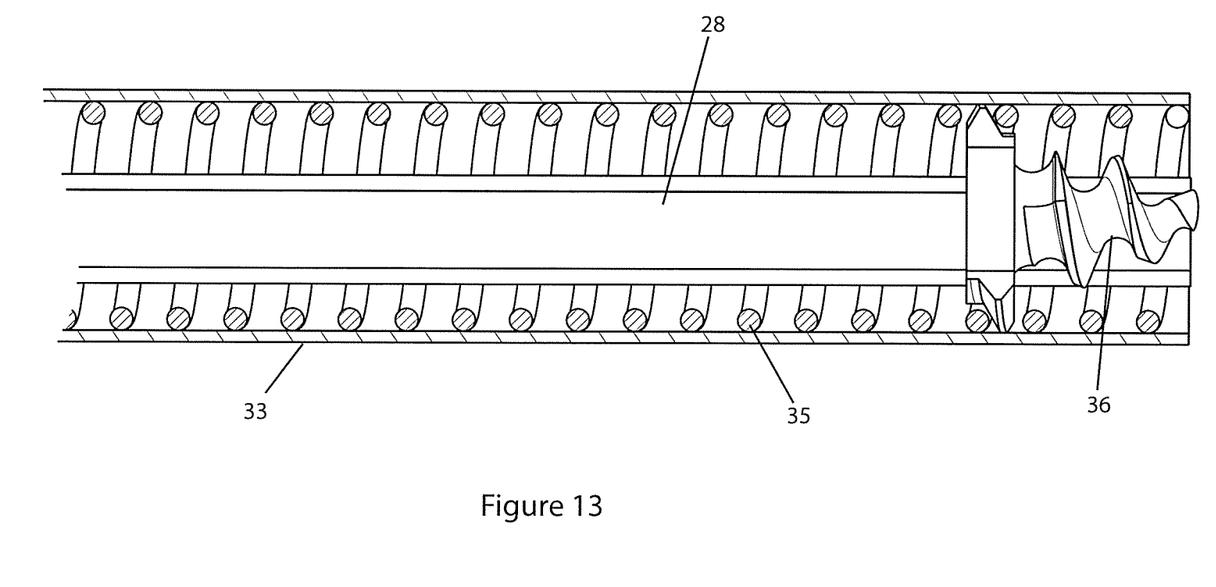
FIG. 13 is a cross section view of the distal end of the device for the delivery of surgical fasteners showing one embodiment of a fastener and its position prior to placement.

As second wheel 12 revolves, crown wheel 26 (attached to second wheel 12) drives shaft 28 through pinion 27. The ratio between crown wheel 26 and pinion 27 can be selected to give shaft 28 the desired number of turns needed to drive one fastener for each complete pull of lever 1. By simply altering the gear ratio between crown wheel 26 and pinion 27, the delivery device may provide one or more additional turns of the fastener for each instance of delivery device actuation. Fasteners are driven by the rotation of shaft 28 that can engage fasteners by a number of methods. By example shown in FIGS. 12 and 13, the shaft 28 can have parallel grooves in the distal end that engage the head(s) of the fasteners 36 thus rotating and driving the fasteners by way of the threaded end 35 of the applicator, such that the fastener while rotated is axially advanced into mesh and tissue. Alternative methods of engaging and advancing a fastener with such a rotating shaft are well known in the art and may be adopted for use with the embodiments contained herein.

One alternate embodiment does not include the one-way clutch 7. In this embodiment first wheel 11 rotates freely with lever 1 in both directions. In this manner energy is only stored in the spring 10 while the handle lever 1 is depressed, and if lever 1 is released, the inputted energy is also released, as mainspring 10 unwinds.

Figure 14:
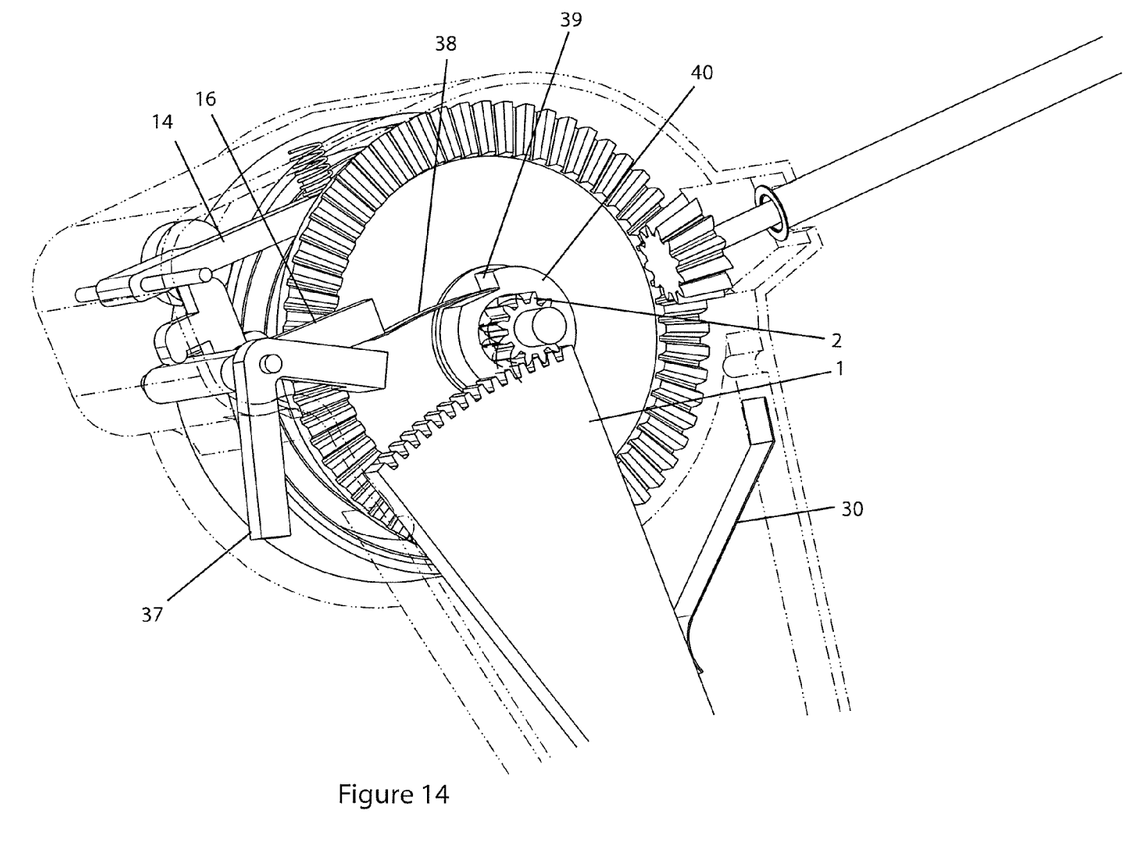
FIG. 14 shows an alternate embodiment using a separate trigger for releasing the stored energy with an interlock prohibiting winding of the spring until the previous wind is discharged.
Figure 15:
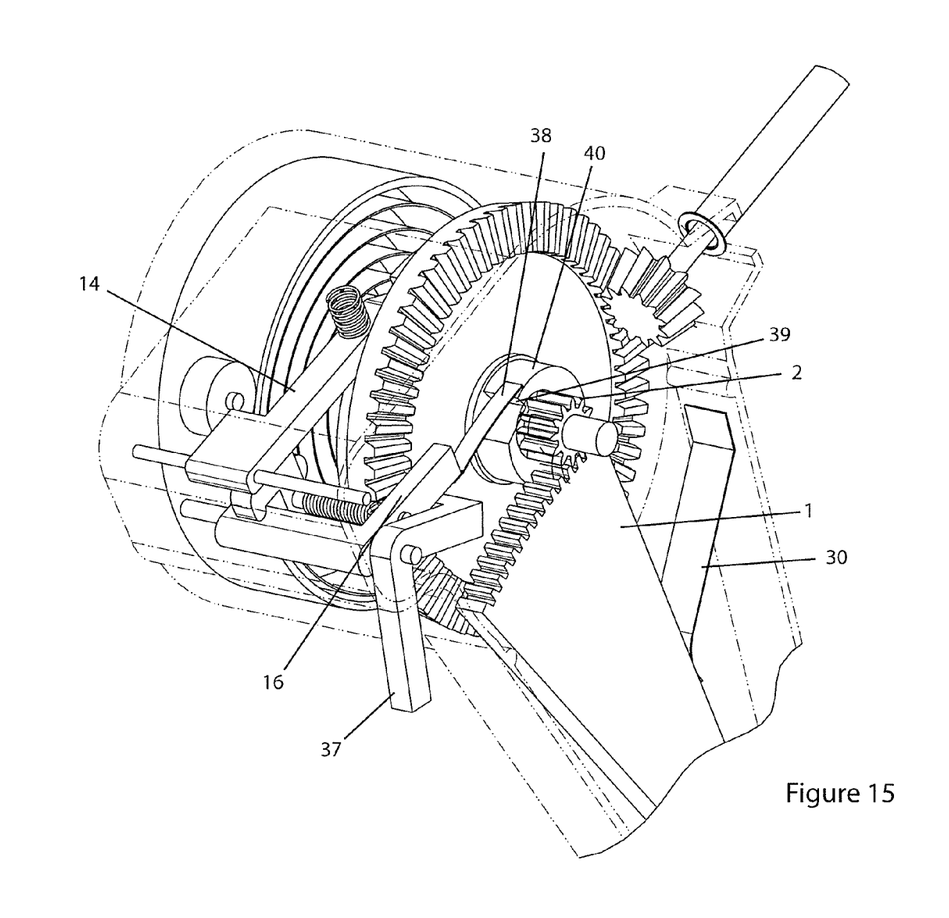
FIG. 15 shows the alternate embodiment of FIG. 14 in the home position ready for winding the resilient element.

Another alternate embodiment, FIG. 14, includes a separately operated trigger 37 that lifts arm 16 to fire one rotation of second wheel 12 after one revolution of first wheel 11 has been applied. An interlock is provided by the interaction of flexible tab 38 with notch 39 on cam 40 to insure that only one revolution of first wheel 11 is permitted for each rotation of second wheel 12. Spring 10 cannot be wound until the previous stroke is discharged. This arrangement allows the operator to wind spring 10 with lever 1 and release the stored spring energy with separate trigger 37 when ready. FIG. 14 shows the device in the ready to deploy state, with spring 10 being previously wound one turn through the action of lever 1. Lever 1 cannot be actuated due to tab 38 stopping the further winding movement of cam 40 that is attached through shaft 9 to first wheel 11. FIG. 15 shows the applicator in the home position, after having applied one fastener and is ready to wind spring 10 by depressing lever 1. Flexible tab 38 retuned to its full length when released by the action of trigger 37 on link 16 and thereby did not reenter notch 39 on cam 40 that remained stationary due to the action of anti-reverse clutch 7 on first wheel 11. With the alternate embodiment without anti-reverse clutch 7, the user would need to hold lever 1 fully depressed while actuating trigger 37.

In another embodiment, one stroke of lever 1 wind spring 10 is sufficient for multiple fastener deployments. Each fastener may then be deployed by separate actuations of trigger 37. Using the separate trigger arrangement allows for pre-winding the spring for multiple fastener deployments, so that the user would not have to wind spring 10 with the action of lever 1 in between each fastener.

Figure 16:
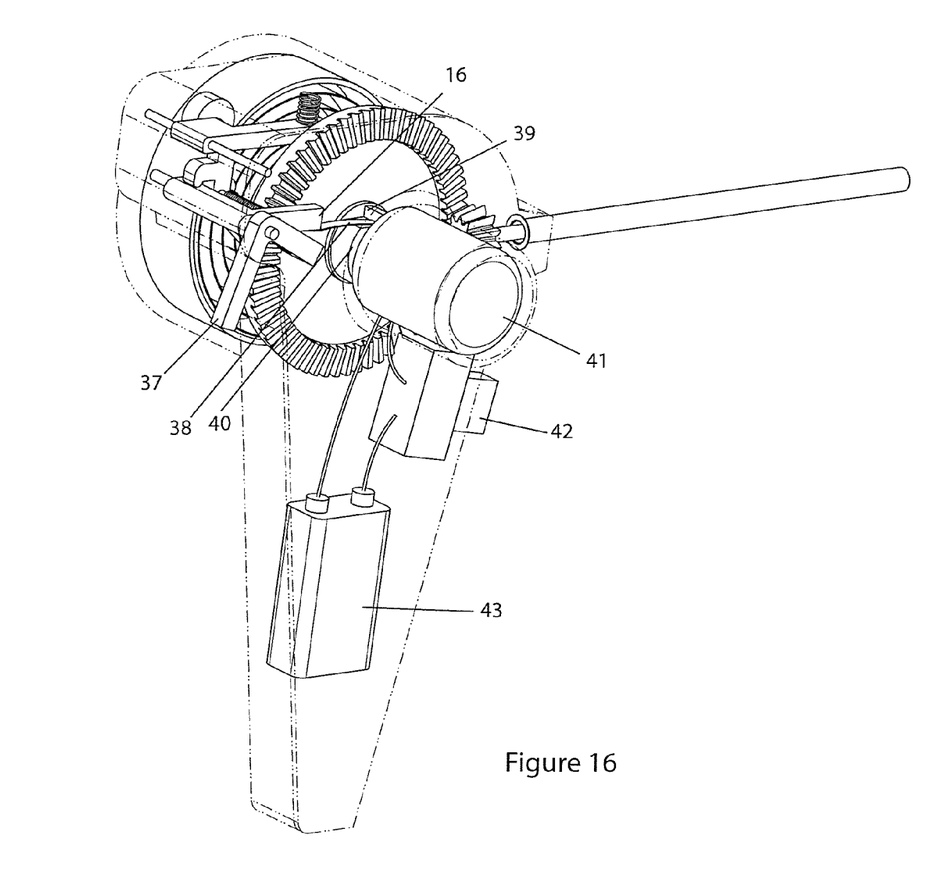
FIG. 16 shows an alternate embodiment for using a motor to wind the spring.

FIG. 16 shows another alternative embodiment that employs a motor 41 to wind spring 10. Actuation of motor 41 through switch 42 causes the motor to rotate shaft 8 which in turn rotates first wheel 11 one turn through the action of surface 4 of tab 3 engaging buttress 6A at the end of slot 5 on first wheel 11. Release of the spring energy to drive one fastener is accomplished as before with the separate trigger 37. The interlock as described previously prevents winding of the spring unless the previous wind has been discharged.

Numerous other embodiments and modifications will be apparent to those skilled in the art and it will be appreciated that the above description of a preferred embodiment is illustrative only. It is not intended to limit the scope of the embodiments contained herein, which are defined by the following claims. Without further elaboration the foregoing will so fully illustrate our invention that others may, by applying current or future knowledge, adopt the same for use under various conditions of service.

What is claimed:

1. A device for the delivery of surgical fasteners comprising:
a lever arranged to pivot on a fulcrum, a first wheel, a second wheel, a one-way clutch mechanism, a resilient element, and a drive mechanism,
wherein said lever is selectively mechanically coupled to said first wheel,
wherein said first wheel is mechanically coupled to a resilient element configured to store energy, wherein said resilient element is also operatively coupled to said second wheel and configured to release said stored energy as rotation of said second wheel,
wherein the rotation of said second wheel is transmitted via said drive mechanism, said drive mechanism configured to deliver at least one surgical fastener into a target site,
wherein, the at least partial depression of said lever stores energy in said resilient element, and said one-way clutch mechanism prevents the release of the stored energy from the resilient element upon release of said lever from the at least partially depressed position.

2. The device of claim 1, wherein said drive mechanism is further configured to deliver the at least one surgical fastener into the target site by imparting of rotational and axial energy to the at least one fastener.

3. The device of claim 1, wherein one complete depression of said lever stores sufficient energy to deploy one surgical fastener into tissue.

4. The device of claim 1, further comprising a trigger for releasing the stored energy.

5. The device of claim 4, wherein one complete depression of the lever stores sufficient energy to deploy more than one surgical fastener.

6. The device of claim 1, wherein release of the stored energy is triggered upon complete depression of said lever.

7. The device of claim 1, wherein upon complete depression of the lever, the release mechanism is triggered before further energy is stored.

8. The device of claim 1, further comprising a handle having an elongate tubular member, for containing a plurality of surgical fasteners, extending distally from the handle.

9. The device of claim 8, wherein the surgical fasteners are iteratively deployable.

10. A method for applying surgical fasteners comprising:
positioning a surgical mesh;
positioning a surgical fastener delivery system comprising:
a lever arranged to pivot on a fulcrum, a first wheel, a second wheel, a one-way clutch mechanism, a resilient element, a drive mechanism, and a handle having an elongate tubular member, wherein said lever is selectively mechanically coupled to said first wheel, wherein said first wheel is mechanically coupled to a resilient element configured to store energy, wherein said resilient element is also operatively coupled to said second wheel and configured to release said stored energy as rotation of said second wheel, wherein the rotation of said second wheel is transmitted via said drive mechanism, said drive mechanism configured to deliver at least one surgical fastener into a target site, wherein, the at least partial depression of said lever stores energy in said resilient element, and said one-way clutch mechanism prevents the release of the stored energy from the resilient element upon release of said lever from the at least partially depressed position; and
an elongate tubular member, containing a plurality of surgical fasteners, extending distally from the handle, and having a distal tip;
wherein the positioning step includes positioning a distal tip of the elongate tubular member against the surgical mesh; and
applying at least one fastener to secure the mesh to a tissue by:
depressing said lever in relation to the handle;
triggering instantaneous release of said stored energy;
converting released energy into a rotational force to cause rotation of one of the plurality of surgical fasteners, whereby said one of the plurality of surgical fasteners penetrates and secures said mesh to a tissue.

11. The method of claim 10, wherein one complete depression of the lever stores sufficient energy to deploy one surgical fastener into said tissue.

12. The method of claim 10, wherein release of the stored energy is triggered upon complete depression of said lever.

13. The method of claim 10, wherein upon complete depression of the lever, the release mechanism is triggered before further energy is stored.

14. A kit comprising:
a device for the delivery of surgical fasteners comprising:
a lever arranged to pivot on a fulcrum, a first wheel, a second wheel, a one-way clutch mechanism, a resilient element, a drive mechanism,
wherein said lever is selectively mechanically coupled to said first wheel,
wherein said first wheel is mechanically coupled to a resilient element configured to store energy, wherein said resilient element is also operatively coupled to said second wheel and configured to release said stored energy as rotation of said second wheel,
wherein the rotation of said second wheel is transmitted via said drive mechanism, said drive mechanism configured to deliver at least one surgical fastener into a target site,
wherein, the at least partial depression of said lever stores energy in said resilient element, and said one-way clutch mechanism prevents the release of the stored energy from the resilient element upon release of said lever from the at least partially depressed position; and
multiple fastener cartridges.

15. The kit of claim 14, wherein the drive mechanism converts stored energy to rotational energy that drives said at least one surgical fastener into tissue.

16. The kit of claim 14, wherein the drive mechanism converts stored energy to rotational energy that drives said at least one surgical fastener into tissue.

* * * * *